US009216415B2

(12) United States Patent
Shenderov et al.

(10) Patent No.: US 9,216,415 B2
(45) Date of Patent: *Dec. 22, 2015

(54) METHODS OF DISPENSING AND WITHDRAWING LIQUID IN AN ELECTROWETTING DEVICE

(75) Inventors: Alexander D. Shenderov, Raleigh, NC (US); Michael G. Pollack, Durham, NC (US)

(73) Assignees: Advanced Liquid Logic, Morrisville, NC (US); Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/006,798

(22) Filed: Jan. 14, 2011

(65) Prior Publication Data

US 2012/0132528 A1 May 31, 2012

Related U.S. Application Data

(63) Continuation of application No. 11/912,912, filed as application No. PCT/US2006/018088 on May 10, 2006.

(60) Provisional application No. 60/679,714, filed on May 11, 2005.

(51) Int. Cl.

*B01L 3/00* (2006.01)
*C12Q 1/68* (2006.01)

(Continued)

(52) U.S. Cl.

CPC ........... *B01L 7/525* (2013.01); *B01L 3/502792* (2013.01); *B01L 2200/0673* (2013.01); *B01L 2300/0654* (2013.01); *B01L 2300/089* (2013.01);

(Continued)

(58) Field of Classification Search

CPC .... B01L 7/525; B01L 3/502792; C12Q 1/686
See application file for complete search history.

(56) References Cited

U.S. PATENT DOCUMENTS

| | | | |
|---|---|---|---|
| 4,390,403 | A | 6/1983 | Batchelder |
| 4,636,785 | A | 1/1987 | Le Pesant |

(Continued)

FOREIGN PATENT DOCUMENTS

| | | | |
|---|---|---|---|
| DE | 10162188 | A1 | 6/2003 |
| EP | 0636413 | A2 | 2/1995 |

(Continued)

OTHER PUBLICATIONS

Yi et al "Soft printing of droplets pre-metered by electrowetting" Sensors & Actuators, Jan. 25, 2004, 114: 347-354.*

(Continued)

*Primary Examiner* — Betty Forman

(74) *Attorney, Agent, or Firm* — Knobbe, Martens, Olson & Bear, LLP

(57) ABSTRACT

The invention provides a method for dispensing liquid, comprising the steps of: (a) positioning a droplet to be dispensed in a gap of an electrowetting device using an electrowetting array; and (b) dispensing the droplet through a hole in a housing or substrate of the electrowetting device. The invention further provides a method for withdrawing liquid comprising the steps of: (a) positioning a droplet to be withdrawn from a gap of an electrowetting device using an electrowetting array; and (b) withdrawing the droplet through a hole in a housing or substrate of the electrowetting device.

20 Claims, 2 Drawing Sheets

(51) Int. Cl.
*C12P 19/34* (2006.01)
*B01L 7/00* (2006.01)

(52) U.S. Cl.
CPC .. *B01L 2300/0864* (2013.01); *B01L 2300/0887* (2013.01); *B01L 2400/0427* (2013.01)

(56) References Cited

U.S. PATENT DOCUMENTS 4,911,782 A 3/1990 Brown
5,038,852 A 8/1991 Johnson et al.
5,176,203 A 1/1993 Larzul
5,181,016 A 1/1993 Lee
5,486,337 A 1/1996 Ohkawa
5,498,392 A 3/1996 Wilding et al.
5,503,803 A 4/1996 Brown
5,525,493 A 6/1996 Hornes et al.
5,720,923 A 2/1998 Haff et al.
5,779,977 A 7/1998 Haff et al.
5,827,480 A 10/1998 Haff et al.
5,871,908 A 2/1999 Henco et al.
6,033,880 A 3/2000 Haff et al.
6,063,339 A 5/2000 Tisone et al.
6,130,098 A 10/2000 Handique et al.
6,180,372 B1 1/2001 Franzen
6,294,063 B1 9/2001 Becker et al.
6,454,924 B2 9/2002 Jedrzejewski et al.
6,565,727 B1 5/2003 Shenderov
6,773,566 B2 8/2004 Shenderov
6,790,011 B1 9/2004 Le Pesant et al.
6,896,855 B1 5/2005 Kohler et al.
6,911,132 B2 6/2005 Pamula et al.
6,924,792 B1 8/2005 Jessop
6,960,437 B2 11/2005 Enzelberger et al.
6,977,033 B2 12/2005 Becker et al.
6,989,234 B2 1/2006 Kolar et al.
7,052,244 B2 5/2006 Fouillet et al.
7,163,612 B2 1/2007 Sterling et al.
7,211,223 B2 5/2007 Fouillet et al.
7,255,780 B2 8/2007 Shenderov
7,328,979 B2 2/2008 Decre et al.
7,329,545 B2 2/2008 Pamula et al.
7,338,760 B2 3/2008 Gong et al.
7,439,014 B2 10/2008 Pamula et al.
7,458,661 B2 12/2008 Kim et al.
7,531,072 B2 5/2009 Roux et al.
7,547,380 B2 6/2009 Velev
7,569,129 B2 8/2009 Pamula et al.
7,579,172 B2 8/2009 Cho et al.
7,641,779 B2 1/2010 Becker et al.
7,727,466 B2 6/2010 Meathrel et al.
7,727,723 B2 6/2010 Pollack et al.
7,763,471 B2 7/2010 Pamula et al.
7,815,871 B2 10/2010 Pamula et al.
7,816,121 B2 10/2010 Pollack et al.
7,822,510 B2 10/2010 Paik et al.
7,851,184 B2 * 12/2010 Pollack et al. ............... 435/91.2
7,901,947 B2 3/2011 Pollack et al.
7,919,330 B2 4/2011 De Guzman et al.
7,922,886 B2 4/2011 Fouillet et al.
7,943,030 B2 5/2011 Shenderov
7,989,056 B2 8/2011 Plissonnier et al.
7,998,436 B2 8/2011 Pollack
8,007,739 B2 8/2011 Pollack et al.
8,041,463 B2 10/2011 Pollack et al.
8,048,628 B2 11/2011 Pollack et al.
8,088,578 B2 * 1/2012 Hua et al. ....................... 435/6.1
8,137,917 B2 * 3/2012 Pollack et al. ............... 435/6.12
8,147,668 B2 4/2012 Pollack et al.
8,221,605 B2 7/2012 Pollack et al.
8,236,156 B2 8/2012 Sarrut et al.
8,287,711 B2 10/2012 Pollack et al.
8,304,253 B2 11/2012 Yi et al.
8,313,698 B2 11/2012 Pollack et al.
8,349,276 B2 1/2013 Pamula et al.
8,388,909 B2 3/2013 Pollack et al.
8,389,297 B2 3/2013 Pamula et al.
8,394,249 B2 3/2013 Pollack et al.
2002/0005354 A1 1/2002 Spence et al.
2002/0036139 A1 3/2002 Becker et al.
2002/0043463 A1 4/2002 Shenderov
2002/0058332 A1 5/2002 Quake et al.
2002/0143437 A1 10/2002 Handique et al.
2003/0049632 A1 3/2003 Edman et al.
2003/0082081 A1 5/2003 Fouillet et al.
2003/0164295 A1 9/2003 Sterling
2003/0183525 A1 10/2003 Elrod et al.
2003/0205632 A1 11/2003 Kim et al.
2004/0007377 A1 1/2004 Fouillet et al.
2004/0031688 A1 2/2004 Shenderov
2004/0055536 A1 3/2004 Kolar et al.
2004/0055891 A1 3/2004 Pamula et al.
2004/0058450 A1 * 3/2004 Pamula et al. ................ 436/150
2004/0180346 A1 9/2004 Anderson et al.
2004/0231987 A1 11/2004 Sterling et al.
2005/0064423 A1 3/2005 Higuchi et al.
2005/0106742 A1 5/2005 Wahl et al.
2005/0142037 A1 6/2005 Reihs
2005/0179746 A1 * 8/2005 Roux et al. ...................... 347/69
2006/0021875 A1 2/2006 Griffith et al.
2006/0054503 A1 3/2006 Pamula et al.
2006/0164490 A1 7/2006 Kim et al.
2006/0194331 A1 8/2006 Pamula et al.
2006/0231398 A1 10/2006 Sarrut et al.
2006/0254933 A1 11/2006 Adachi et al.
2007/0023292 A1 2/2007 Kim et al.
2007/0037294 A1 2/2007 Pamula et al.
2007/0045117 A1 3/2007 Pamula et al.
2007/0064990 A1 3/2007 Roth
2007/0086927 A1 4/2007 Natarajan et al.
2007/0207513 A1 9/2007 Sorensen et al.
2007/0217956 A1 9/2007 Pamula et al.
2007/0241068 A1 10/2007 Pamula et al.
2007/0242105 A1 10/2007 Srinivasan et al.
2007/0242111 A1 10/2007 Pamula et al.
2007/0243634 A1 10/2007 Pamula et al.
2007/0267294 A1 11/2007 Shenderov
2007/0275415 A1 11/2007 Srinivasan et al.
2008/0006535 A1 1/2008 Paik et al.
2008/0038810 A1 2/2008 Pollack et al.
2008/0044893 A1 2/2008 Pollack et al.
2008/0044914 A1 2/2008 Pamula et al.
2008/0050834 A1 2/2008 Pamula et al.
2008/0053205 A1 3/2008 Pollack et al.
2008/0105549 A1 5/2008 Pamela et al.
2008/0124252 A1 5/2008 Marchand et al.
2008/0138815 A1 6/2008 Brown et al.
2008/0142376 A1 6/2008 Fouillet et al.
2008/0151240 A1 6/2008 Roth
2008/0153091 A1 6/2008 Brown et al.
2008/0160525 A1 7/2008 Brown et al.
2008/0166793 A1 7/2008 Beer et al.
2008/0169184 A1 7/2008 Brown et al.
2008/0171324 A1 7/2008 Brown et al.
2008/0171325 A1 7/2008 Brown et al.
2008/0171326 A1 7/2008 Brown et al.
2008/0171327 A1 7/2008 Brown et al.
2008/0171382 A1 7/2008 Brown et al.
2008/0213766 A1 9/2008 Brown et al.
2008/0247920 A1 10/2008 Pollack et al.
2008/0264797 A1 10/2008 Pamula et al.
2008/0274513 A1 * 11/2008 Shenderov et al. .......... 435/91.2
2008/0302431 A1 12/2008 Marchand et al.
2009/0014394 A1 1/2009 Yi et al.
2009/0042319 A1 2/2009 De Guzman et al.
2009/0053726 A1 2/2009 Owen et al.
2009/0142564 A1 6/2009 Plissonnier et al.
2009/0155902 A1 6/2009 Pollack et al.
2009/0192044 A1 7/2009 Fouillet
2009/0260988 A1 10/2009 Pamula et al.
2009/0263834 A1 10/2009 Sista et al.
2009/0280251 A1 11/2009 De Guzman et al.
2009/0280475 A1 11/2009 Pollack et al.
2009/0280476 A1 11/2009 Srinivasan et al.

(56) References Cited

U.S. PATENT DOCUMENTS

| | | | |
|---|---|---|---|
| 2009/0291433 | A1 | 11/2009 | Pollack et al. |
| 2010/0025242 | A1 | 2/2010 | Pamula et al. |
| 2010/0096266 | A1 | 4/2010 | Kim |
| 2010/0116640 | A1 | 5/2010 | Pamula et al. |
| 2010/0140093 | A1 | 6/2010 | Pamula et al. |
| 2010/0143963 | A1 | 6/2010 | Pollack |
| 2010/0258441 | A1 | 10/2010 | Sista et al. |
| 2010/0279374 | A1 | 11/2010 | Sista et al. |
| 2011/0100823 | A1 | 5/2011 | Pollack et al. |
| 2011/0114490 | A1 | 5/2011 | Pamula et al. |
| 2011/0118132 | A1 | 5/2011 | Winger et al. |
| 2011/0180571 | A1 | 7/2011 | Srinivasan et al. |
| 2011/0186433 | A1 | 8/2011 | Pollack et al. |
| 2011/0203930 | A1 | 8/2011 | Pamula et al. |
| 2011/0209998 | A1 | 9/2011 | Shenderov |
| 2012/0018306 | A1 | 1/2012 | Srinivasan et al. |
| 2012/0132528 | A1 | 5/2012 | Shenderov et al. |
| 2012/0165238 | A1 | 6/2012 | Pamula et al. |

FOREIGN PATENT DOCUMENTS

| | | | |
|---|---|---|---|
| GB | WO2004073863 | A2 | 9/2004 |
| JP | 2006329899 | A | 12/2006 |
| JP | 2006329904 | A | 12/2006 |
| WO | WO9917093 | A1 | 4/1999 |
| WO | WO9954730 | A1 | 10/1999 |
| WO | 0069565 | A1 | 11/2000 |
| WO | 0073655 | A1 | 12/2000 |
| WO | 0207503 | A1 | 1/2002 |
| WO | 2004029585 | A1 | 4/2004 |
| WO | 2004030820 | | 4/2004 |
| WO | 2005047696 | A1 | 5/2005 |
| WO | 2006013303 | A1 | 2/2006 |
| WO | 2006070162 | A1 | 7/2006 |
| WO | 2006081558 | | 8/2006 |
| WO | 2006124458 | A2 | 11/2006 |
| WO | 2006127451 | A2 | 11/2006 |
| WO | 2006138543 | | 12/2006 |
| WO | 2007003720 | A1 | 1/2007 |
| WO | 2007048111 | | 4/2007 |
| WO | 2007120240 | A2 | 10/2007 |
| WO | 2007120241 | A2 | 10/2007 |
| WO | 2007123908 | A2 | 11/2007 |
| WO | 2008051310 | A2 | 5/2008 |

OTHER PUBLICATIONS

Aldrich et al., "PathoFinder: Microscale PCR Based Virus Detection," Yale Department of Engineering Design Course Report, Dec. 2003.
Jie Ding, "System level architectural optimization of semi-reconfigurable microfluidic system," M.S. Thesis, Duke University Dept of Electrical Engineering, 2000.
Shih-Kang Fan, "Digital Microfluidics by Cross-Reference EWOD Actuation: Principle, Device, and System," PhD Dissertation, University of California Dept. of Mechanical Engineering, 2003.
Hyejin Moon, "Electrowetting-On-Dielectric Microfluidics: Modeling, Physics, and MALDI Application," Ph.D. Dissertation, University of California Dept. of Mechanical Engineering, published Aug. 2006.
Pollack et al., "Electrowetting-Based Actuation of Droplets for Integrated Microfluidics," Lab on a Chip (LOC), vol. 2, pp. 96-101, 2002.
Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.
Altti Torkkeli, "Droplet microfluidics on a planar surface," Doctoral Dissertation, Department of Electrical Engineering, Helsinki University of Technology (Oct. 3, 2003).
Chang-Jin Kim et al., "Electrowetting-Driven Micropumping," UCLA Invention Report, Amendment, Declaration including Invention Report, Petition for Extension of Time, and Authorization to Charge Deposit, submitted to USPTO on Feb. 4, 2005.
Cho et al., "Towards Digital Microfluidic Circuits: Creating, Transporting, Cutting and Merging Liquid Droplets by Electrowetting-Based Actuation," Proc. IEEE/Micro Electro Mechanical Systems Conference, pp. 32-35, 2002.
J.A. Schwartz, "Dielectrophoretic Approaches to Sample Preparation and Analysis," The University of Texas, Dissertation, Dec. 2001.
Masao Washizu, "Electrostatic Actuation of Liquid Droplets for Micro-Reactor Applications", IEEE Industry Applications Society Annual Meeting, pp. 1867-1873, Oct. 5-9, 1997.
Chatterjee, Debalina. "Lab on a Chip Applications with a Digital Microfluidic Platform," UCLA Dissertation 2008, UMI Microform No. 3342975.
Vinet, F., et al., "Microarrays and microfluidic devices; miniaturized systems for biological analysis," Microelectronic Engineering 61-62 (2002) 41-47.
Seyrat E, Hayes RA, "Amorphous fluoropolymers as insulators for reversible low-voltage electrowetting," Journal of Applied Physics, vol. 90 (3): pp. 1383-1386, Aug 1, 2001.
Juergen Pipper et al., "Clockwork PCR Including Sample Preparation," Angew. Chem. Int. Ed., vol. 47, pp. 3900-3904, 2008.
Olivier Raccurt et al., "On the influence of surfactants in electrowetting systems," J. Micromech. Microeng., vol. 17, pp. 2217-2223 (2007).
Jean-Maxime Roux and Yves Fouillet, "3D droplet displacement in microfluidic systems by electrostatic actuation," Sensors and Actuators A, vol. 134, Issue 2, pp. 486-493, Mar. 15, 2007.
Aaron R. Wheeler, "Putting Electrowetting to Work," Science, vol. 322, No. 5901, pp. 539-540, Oct. 24, 2008.
T.H. Zhang, K. Chakrabarty, R.B. Fair, "Behavioral modeling and performance evaluation of microelectrofluidics-based PCR systems using SystemC", IEEE Transactions on Computer-Aided Design of Integrated Circuits & Systems, vol. 23 (6): pp. 843-858, Jun. 2004.
Fair, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.
Colgate E, Matsumoto H, "An Investigation of Electrowetting-based Microactuation," Journal of Vacuum Science & Technology A-Vacuume Surfaces and Films, V. 8 (4): pp. 3625-3633, Jul.-Aug. 1990.
Pollack et al., "Investigation of electrowetting-based microfluidics for real-time PCR applications," 7th Int'l Conference on Micro Total Analysis Systems (μTAS), 2003.
Pollack et al., Proceedings of Utas 2003-Seventh International Conference on Micro Total Analysis Systems: pp. 619-622 (2003).
Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.
Tuckerman, D.B. and R.F.W. Pease, "High-Performance Heat Sinking for VLSI, "IEEE Electron Device Letters, 1981, pp. 126-129.
Batchelder, J.S., "Dielectrophoretic manipulator," Review of Scientific Instruments, vol. 54, 1983, pp. 300-302.
Manz, A., N. Graber, and H.M. Widmer, "Miniaturized Total Chemical Analysis Systems: a Novel Concept for Chemical Sensing," Sensors and Actuators B: Chemical, 1990, pp. 244-248.
Welters, W.J.J. and L.G.J. Fokkink, "Fast Electrically Switchable Capillary Effects," Langmuir, vol. 14, Mar. 1998, pp. 1535-1538.
McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.
A. Wego, S. Richter, L. Pagel, "Fluidic microsystems based on printed circuit board technology," Journal of Micromechanics and Microengineering, vol. 11, No. 5, pp. 528-531 (Sep. 2001).
Moon H, Cho Sk, Garrell RL, et al., "Low voltage electrowetting-on-dielectric," Journal of Applied Physics, vol. 92 (7): pp. 4080-4087, Oct. 1, 2002.
Locascio, L.E., et al. "Polymer microfluidic devices," Talanta, vol. 56, Feb. 2002, pp. 267-287.
Garrell, R.L. et al., "Preventing Biomolecular Adsorption in Electrowetting-Based Biofluidic Chips," Analytical Chemistry, vol. 75, Oct. 2003, pp. 5097-5102.

(56) References Cited

OTHER PUBLICATIONS

P.Y. Chiou, H. Moon, H. Toshiyoshi, C.-J. Kim, and M.C. Wu, "Light actuation of liquid by optoelectrowetting," Sensors and Actuators A: Physical, vol. 104, May. 2003, pp. 222-228.
Squires, T.M. and S.R. Quake, "Microfluidics: Fluid physics at the nanoliter scale," Reviews of Modern Physics, vol. 77, Oct. 2005, pp. 977-1-26.
Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.
Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump. ," Lab on a chip, vol. 5, Mar. 2005, pp. 12617-12622.
Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.
Cooney, C.G., C-Y. Chen, M.R. Emerling, A Nadim, and J.D. Sterling, Microfluidics and Nanofluidics, vol. 2 Mar. 2006, pp. 435-446.
Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.
M.Madou, J. Zoval, G. Jia, H. Kido, J. Kim, "Lab on a CD," Annual Review of Biomedical Engineering, vol. 8, pp. 601-628, 2006.
Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.
Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.
Whitesides, G.M., "The origins and the future of microfluidics," Nature, vol. 442, 2006, pp. 368-373.
Office Action dated Jun. 11, 2010 from co-pending U.S. Appl. No. 11/912,913.
Response to Office Action dated Aug. 3, 2010 from co-pending U.S. Appl. No. 11/912,913.
Office Action dated Nov. 1, 2010 from co-pending U.S. Appl. No. 11/912,913.
Response to Office Action dated Nov. 4, 2010 from co-pending U.S. Appl. No. 11/912,913.
Office Action dated Dec. 15, 2010 from co-pending U.S. Appl. No. 11/912,913.
Response to Office Action dated Dec. 29, 2010 from co-pending U.S. Appl. No. 11/912,913.
Office Action dated Mar. 18, 2011 from co-pending U.S. Appl. No. 11/912,913.
Chin, C.D., V. Linder, and S.K. Sia, "Lab-on-a-chip devices for global health: past studies and future opportunities.," Lab on a Chip, vol. 7, Jan. 2007, pp. 41-57.
Baviere, R., J. Boutet, and Y. Fouillet, "Dynamics of droplet transport induced by electrowetting actuation," Microfluidics and Nanofluidics, vol. 4, May. 2007, pp. 287-294.
Zhang et al., "System Performance Evaluation with SystemC for Two PCR Microelectrofluidic Systems," Proceedings of the International Conference on Modeling and Simulation of Microsystems, San Juan, PR, pp. 48-53, Apr. 2002.
Burns, et al., "An Integrated Nanoliter DNA Analysis Device." Science vol. 282, 1998, pp. 484-487.
Chakrabarty et al., "Design Automation Challenges for Microfluidics-Based Biochips", DTIP of MEMS & MOEMS, Montreux, Switzerland, Jun. 1-3, 2005.
Chakrabarty et al., "Design Automation for Microfluidics-Based Biochips", ACM Journal on Engineering Technologies in Computing Systems , 1(3), Oct. 2005, 186-223.
Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.
Chatterjee et al., "Droplet-Based Microfluidics with Nonaqueous Solvents and Solutions.," Lab on a Chip, vol. 6, Feb. 2006, pp. 199-206.
Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Load", Sensors and Actuators, vol. 73, Issues 1-2, Mar. 1999, pp. 30-36.
Chiou et al. "A Closed-Cycle Capillary Polymerase Chain Reaction Machine" Anal. Chem. vol. 73, 2001, pp. 2018-2021.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Fair et al., "A Micro- Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair et al., "Chemical and biological pathogen detection in a digital microfluidic platform", DARPA Workshop on Microfluidic Analyzers for DoD and National Security Applications, Keystone, CO, 2006.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fukuba et al., 'Microfabricated Flow-Through Device for DNA Amplification—Towards in Situ Gene Analysis' Chemical Engineering Journal vol. 101, No. 1-3, Aug. 1, 2004, pp. 151-156.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99/3800, 30th AIAA Fluid Dynamics Conference, Norfolk, VA, (Invited lecture), Jun. 1999, pp. 1-6.
Kopp et al., "Chemical amplification: Continuous-flow PCR on a chip", Science vol. 280, 1998, pp. 1046-1048.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.
Liu et al., 'A Nanoliter Rotary Device for Polymerase Chain Reaction' Electrophoresis vol. 23, 2002, pp. 1531-1536.
Nakano et al., High Speed Polymerase Chain Reaction in Constant Flow, Biosci. Biotechnol. Biochem. vol. 58, 1994, pp. 349-352.

(56) References Cited

OTHER PUBLICATIONS

Paik, "Adaptive Hot-Spot Cooling of Integrated Circuits Using Digital Microfluidics", Dissertation, Dept. of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006,I-16.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid- State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Droplet-based microfluidic lab-on-a-chip for glucose detection", Analytica Chimica Acta, vol. 507, No. 1, 2004, 145-150.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published on-line, May 2004, 3229-3235.
Wang et al., "Droplet-based micro oscillating-flow PCR chip", J. Micromechanics and Microengineering, vol. 15, 2005, 1369-1377.
Xu et al., "Droplet-Trace-Based Array Partitioning and a Pin Assignment Algorithm for the Automated Design of Digital Microfluidic Biochips", CODES, 2006, 112-117.
Yao et al., "Spot Cooling Using Thermoelectric Microcooler", Proc. 18th Int. Thermoelectric Conf, Baltimore, VA, pp. 256-259, Aug. 1999.
Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.
Yi, "Soft Printing of Biological Liquids for Micro-arrays: Concept, Principle, Fabrication, and Demonstration", Ph.D. dissertation, UCLA, 2004.
Yi et al., "Soft Printing of Droplets Digitized by Electrowetting", Transducers 12th Intl Conf. on Solid State Sensors, Actuators and Microsystems, Boston, Jun. 8-12, 2003, 1804-1807.
Yi et al., "Soft Printing of Droplets Pre-Metered by Electrowetting", Sensors and Actuators A: Physical, vol. 114, Jan. 2004, 347-354.
Zeng et al., "Actuation and Control of Droplets by Using Electrowetting-on-Dielectric", Chin. Phys. Lett., vol. 21(9), 2004, 1851-1854.
Zhang et al., "Behavioral Modeling and Performance Evaluation of Microelectrofluidics-Based PCR Systems Using SystemC", IEEE Transactions on Computer-Aided Design of Integrated Circuits and Systems, 2004, vol. 23, pp. 843-858.

(56) References Cited

OTHER PUBLICATIONS

International Search Report dated Oct. 3, 2007 from PCT International Application No. PCT/US2006/018088.
Weaver, "Application of Magnetic Microspheres for Pyrosequencing on a Digital Microfluidic Platform", Department of Electrical and Computer Engineering, Duke University, 2005.
Bu, et al., Design and theoretical evaluation of a novel microfluidic device to be used for PCR, J. Micromech. Microeng. 13 (Jun. 13, 2003), pp. S125-S130.
Nakano, et al., Single-molecule PCR using water-in-oil emulsion, Research Gate, Journal of Biotechnology, May 2003.
Su, et al., Concurrent testing of droplet-based microfluidic systems for multiplexed biomedical assays, Test Conference, 2004. Proceedings. ITC 2004. International, Oct. 28, 2004, pp. 883-892.
Wang, et al., Droplet based micro oscillating flow-through PCR Chip, MEMS 2004: $17^{th}$ IEEE International Conference on Micro Electro Mechanical Systems, pp. 280-283, Jan. 29, 2004.

* cited by examiner

METHODS OF DISPENSING AND WITHDRAWING LIQUID IN AN ELECTROWETTING DEVICE

RELATED APPLICATIONS

In addition to the patent applications cited herein, each of which is incorporated herein by reference, this application is a continuation of and incorporates by reference U.S. patent application Ser. No. 11/912,913, entitled "Method and Device for Conducting Biochemical or Chemical Reactions at Multiple Temperatures" filed on Oct. 29, 2007, the application of which claims priority to and incorporates by reference related International Application No. PCT/US2006/018088, entitled "Method and Device for Conducting Biochemical or Chemical Reactions at Multiple Temperatures" filed on May 10, 2006, which claims the benefit of U.S. Provisional Application No. 61/679,714, entitled "Method and Device for Conducting Biochemical or Chemical Reactions at Multiple Temperatures" filed May 11, 2005, the entirety of which is incorporated herein by reference.

GRANT INFORMATION

This invention was made with Government support awarded by the United States Army Medical Research Acquisition Activity on behalf of the United States Department of Homeland Security Advanced Research Projects Agency pursuant to Other-Transaction-for-Prototype Agreement Number W81XWH-04-9-0019 (HSARPA Order No. TTA-1-103). The United States has certain rights in the invention.

FIELD OF THE INVENTION

The present invention generally relates to methods of dispensing and/or withdrawing liquids. In particular, the present invention is directed to methods of dispensing and/or withdrawing liquids in an electrowetting device.

BACKGROUND OF THE INVENTION

The temperature dependence of biochemical and chemical reaction rates poses a particular challenge to efforts to improve reaction efficiency and speed by miniaturization. A time-domain approach, whereby not only the reaction volume but also the entire housing is kept at a desired temperature, is only suitable for isothermal conditions. If temperature needs to be changed or cycled in a rapid and controlled manner, the added thermal mass of the housing limits the rate and/or precision that can be achieved.

In the space-domain approach (see, e.g., Kopp, M. U., de Mello, A. J., Manz, A., Science 1998, 280, 1046-1048; Burns, M. A., Johnson, B. N., Bralunansandra, S. N., Handique, K., Webster, J. R., Krishman, M., Sammarco, T. S., Man, P. M., Jones, D., Heldsinger, D., Mastrangelo, C. H., Burke, D. T., Science 1998, 282, 484-487; Chiou, J., Matsudaira, P., Sonn, A., Ehrlich, D., Anal. Chem. 2001, 73, 2018-2021; and Nakano, H., Matsuda, K., Yohda, M., Nagamune, T., Endo, I., Yamane, T., Biosci. Biotechnol. Biochem. 1994, 58, 349-352), different parts of the reaction housing are kept at different temperatures, and reaction volume is brought in thermal contact with a desired part of the housing to keep it at the temperature of that part. If necessary, the reaction volume can then be moved to a different part of the housing to change the temperature; and, depending on the trajectory of the reaction volume, the temperature profile of it can be adjusted or cycled as desired. To date, most of the implementations of the space-domain dynamic thermal control have been directed to miniaturized PCR thermocycling. Continuous meandering or spiral channels laid across temperature zones have been demonstrated for continuous flowthrough amplification (see, e.g., Fukuba T, Yamamoto T, Naganuma T, Fujii T Microfabricated flow-through device for DNA amplification—towards in situ gene analysis CHEMICAL ENGINEERING JOURNAL 101 (1-3): 151-156 Aug. 1, 2004); direct-path arrangements with a reaction slug moving back and forth have been described (see, e.g., Chiou, J., Matsudaira, P., Sonn, A., Ehrlich, D., Anal. Chem. 2001, 73, 2018-2021); and finally, cycling of an individual reaction through a loop has been demonstrated (see, e.g., Jian Liu Markus Enzelberger Stephen Quake A nanoliter rotary device for polymerase chain reaction Electrophoresis 2002, 23, 1531-1536).

The existing devices do not provide for passage of the reaction volume through a detection site during each thermal cycle, which would provide a real-time PCR capability. Nor do they employ a multitude of parallel channels, each containing multiple reaction volumes, to improve throughput.

BRIEF DESCRIPTION OF THE INVENTION

In one aspect, a method for conducting dispensing liquid is disclosed. The method including the steps of: (a) positioning a droplet to be dispensed in a gap of an electrowetting device using an electrowetting array; and (b) dispensing the droplet through a hole in a housing or substrate of the electrowetting device. The method may include using pressure, suction, a capillary, or a pipette for dispensing the droplet through the hole. The droplet may include a reaction droplet, wherein the droplet may include DNA and/or PCR reagents. The droplet may also include a reaction droplet that has been subjected to thermal cycling, wherein the thermal cycling may be effected by moving, using the electrowetting array, the reaction droplet through at least two reaction zones.

In another aspect, a method for withdrawing liquid is disclosed. The method including the steps of: (a) positioning a droplet to be withdrawn from a gap of an electrowetting device using an electrowetting array; and (b) withdrawing the droplet through a hole in a housing or substrate of the electrowetting device. The method may include using pressure, suction, a capillary, or a pipette for dispensing the droplet through the hole. The droplet may include a reaction droplet, wherein the droplet may include DNA and/or PCR reagents. The droplet may also include a reaction droplet that has been subjected to thermal cycling, wherein the thermal cycling may be effected by moving, using the electrowetting array, the reaction droplet through at least two reaction zones.

DETAILED DESCRIPTION OF THE INVENTION

The present invention relates to methods and devices for conducting chemical or biochemical reactions that require multiple reaction temperatures. The methods involve moving one or more reaction droplets or reaction volumes through various reaction zones having different temperatures on a microfluidics apparatus. The devices comprise a microfluidics apparatus comprising appropriate actuators capable of moving reaction droplets or reaction volumes through the various reaction zones.

Methods and Devices Using Electrowetting

In one embodiment, the devices comprise an electrowetting array comprising a plurality of electrowetting electrodes, and the method involves using electrowetting to move one or more reaction droplets through various reaction zones on the electrowetting array having different temperatures in order to conduct the reaction.

The electrowetting array of the device may comprise one or more reaction paths that travel through at least two reaction zones of the device. Each reaction zone may be maintained at a separate temperature in order to expose the reaction droplets to the desired temperatures to conduct reactions requiring multiple reaction temperatures. Each reaction path may comprise, for example, a plurality of electrodes on the electrowetting array that together are capable of moving individual droplets from one electrode to the next electrode such that the reaction droplets may be moved through the entire reaction path using electrowetting actuation. Electrowetting arrays, electrowetting electrodes, and devices incorporating the same that may be used include those described in U.S. Pat. Nos. 6,565,727 and 6,773,566 and U.S. Patent Application Publication Nos. 2004/0058450 and 2004/0055891, the contents of which are hereby incorporated by reference herein.

Figure 1:
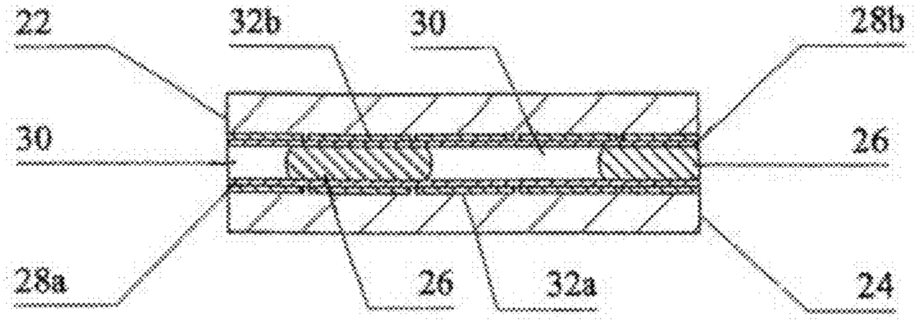
FIG. 1 illustrates a cross section of a portion of one embodiment of a device for conducting chemical or biochemical reactions that require multiple reaction temperatures.

Devices that may be used for conducting reactions requiring multiple reaction temperatures typically comprise a first, flat substrate and a second, flat substrate substantially parallel to the first substrate. A plurality of electrodes that are substantially planer are typically provided on the first substrate. Either a plurality of substantially planar electrodes or one large substantially planer electrode are typically provided on the second substrate. Preferably, at least one of the electrode or electrodes on either the first or second substrate are coated with an insulator. An area between the electrodes (or the insulator coating the electrodes) on the first substrate and the electrodes or electrode (or the insulator coating the electrode(s)) on the second substrate forms a gap that is filled with filler fluid that is substantially immiscible with the liquids that are to be manipulated by the device. Such filler fluids include air, benzenes, or a silicone oil. In some embodiments, the gap is from approximately 0.01 mm to approximately 1 mm, although larger and smaller gaps may also be used. The formation and movement of droplets of the liquid to be manipulated are controlled by electric fields across the gap formed by the electrodes on opposite sides of the gap. FIG. 1 shows a cross section of a portion of one embodiment of a device for conducting chemical or biochemical reactions that require multiple reaction temperatures, with the reference numerals referring to the following: 22-first substrate; 24-second substrate; 26-liquid droplet; 28*a* and 28*b*-hydrophobic insulating coatings; 30-filler fluid; 32*a* and 32*b*-electrodes.

Other devices comprising electrodes on only one substrate (or devices containing only one substrate) may also be used for conducting reactions requiring multiple reaction temperatures. U.S. Patent Application Publication Nos. 2004/0058450 and 2004/0055891, the contents of which are hereby incorporated by reference herein, describe a device with an electrowetting electrode array on only one substrate. Such a device comprises a first substrate and an array of control electrodes embedded thereon or attached thereto. A dielectric layer covers the control electrodes. A two-dimensional grid of conducting lines at a reference potential is superimposed on the electrode array with each conducting line (e.g., wire or bar) running between adjacent drive electrodes.

Each reaction path of the devices for conducting chemical or biochemical reactions includes at least two reaction zones. The reaction zones are maintained at specified temperatures such that reactions requiring multiple reaction temperatures may be conducted. The reaction droplet or droplets are moved through (or allowed to remain in) each reaction zone for an appropriate time according to the specific reaction being performed. The temperatures in the reaction zones are maintained at a substantially constant temperature using any type of heating or cooling, including, for example, resistive, inductive, or infrared heating. The devices for conducting the reactions may further comprise the mechanisms for generating and maintaining the heat or cold needed to keep the reaction zones at a substantially constant temperature.

The devices for conducting chemical or biochemical reactions may optionally have a detection site positioned in or after the reaction paths. In one embodiment, the device comprises a detection site after the last reaction zone in each reaction path. The detection site, which is also part of the electrowetting array of the device, may be designed such that detection of indicia of the reaction (e.g., a label indicating that the reaction occurred or did not occur) or detection of an analyte in the reaction droplet (for quantitation, etc.) may be detected at the detection site. For example, the detection site may comprise a transparent or translucent area in the device such that optical indicia of a feature of the reaction may be optically or visually detected. In addition, a detector may be positioned at the detection site such that the reaction indicia may be detected with or without a transparent or translucent area. Translucent or transparent detection sites may be constructed using a substrate made from, for example, glass or plastic and an electrode made from, for example, indium tin oxide or a thin, transparent metal film. Reaction indicia may comprise, for example, fluorescence, radioactivity, etc., and labels that may be used include fluorescent and radioactive labels. In addition, the detection site may contain bound enzymes or other agents to allow detection of an analyte in the reaction droplets.

As stated above, the reaction path or paths of the device may comprise an array of electrowetting electrodes. In addition, the reaction paths may further comprise a conduit or channel for aiding in defining the fluid path. Such channels or conduits may be part of the electrowetting electrodes themselves, may be part of an insulating coating on the electrodes, or may be separate from the electrodes.

The reaction paths may have various geometrical configurations. For example, the reaction paths may be a circular path comprising at least two reaction zones, a linear path that crosses at least two reaction zones, or other shaped paths. In addition, the devices may comprise an array of electrowetting electrodes that includes multiple possible reaction paths and multiple reaction zones such that the device may be reconfigured for various reactions.

The device may also comprise a return path from the end of the reaction path or from the detection site (if the device includes a detection site after the end of the reaction path) to the beginning of the same reaction path (or to a new, identical reaction path) such that multiple cycles of the reaction may be conducted using the same reagents. That is, the device may contain a return path such that multiple reaction cycles may be conducted using a loop path or a meandering path for the total path of the reaction droplets. As with the reaction path and the detection site, the return path comprises one or more electrowetting electrodes and is part of the electrowetting array of the device. The return path may include a channel or conduit for aiding in defining the fluid path. The return path may go through one or more of the reaction zones or may entirely bypass the reaction zones. In addition, the return path may have a substantially constant temperature (different from or identical to one of the temperatures maintained in the reaction zones) that is maintained by appropriate heating or cooling mechanisms. In addition, the return path may be operated such that reaction droplets are returned to the beginning of the same or a new reaction path faster than the time the reaction droplets spend in the reaction path.

When multiple reaction paths are contained in a device, there may be multiple return paths (e.g., one return path for each reaction path) or there may be less return paths than reaction paths (e.g., only one return path). When there are less return paths than reaction paths, the droplets may be manipulated on the electrowetting array such that the reaction droplets that traveled through a particular path on the first reaction cycle are returned to the identical reaction path for the second reaction cycle, therefore allowing results of each progressive cycle for a particular reaction droplet to be compared to the results of the previous cycles for the same reaction droplet.

In other embodiments, the reaction droplets may be moved to the beginning of the same reaction path without a return path in order to perform cycles of the same reaction. Such a return path may not be needed where the reaction path and any detection site form a loop, or where the reaction path and any detection site do not form a loop (e.g., a linear path) and the reaction droplets are moved in the opposite direction along the same path to return them to the beginning of the same reaction path. The devices comprising an electrowetting array are capable of moving the reaction droplets both unidirectionally in the array for some reactions as well as bidirectionally in a path, as needed. In addition, such devices may be capable of moving reaction droplets in any combination of directions in the array needed to perform a particular reaction and such devices are not limited to linear movement in the electrowetting arrays.

The device may also comprise appropriate structures and mechanisms needed for dispensing liquids (e.g., reaction droplets, filling liquids, or other liquids) into the device as well as withdrawing liquids (e.g., reaction droplets, waste, filling liquid) from the device. Such structures could comprise a hole or holes in a housing or substrate of the device to place or withdraw liquids from the gap in the electrowetting array. Appropriate mechanisms for dispensing or withdrawing liquids from the device include those using suction, pressure, etc., and also include pipettes, capillaries, etc. In addition, reservoirs formed from electrowetting arrays as well as drop meters formed from electrowetting arrays, for example, as described in U.S. Pat. No. 6,565,727, may also be used in the devices described herein.

The methods of conducting chemical or biochemical reactions that require multiple reaction temperatures comprise providing at least one reaction droplet to an electrowetting array of a device described herein and then conducting the reaction by moving, using electrowetting, the at least one reaction droplet through the at least two reaction zones. The at least two reaction zones are maintained at the different temperatures needed for the reaction. If desired, the reaction may be repeated with the same reaction droplet by again moving, using electrowetting, the at least one reaction droplet through the at least two reaction zones. Such repetition may be desired where multiple reaction cycles are needed or preferred for a particular reaction.

The reaction droplet or droplets comprise the reagents needed to conduct the desired reaction, and the reaction droplets (including any sample to be tested) may be prepared outside of the device or may be prepared by mixing one or more droplets in the device using the electrowetting array. In addition, further reagents may be added to the reaction droplet (e.g., by mixing a new reaction droplet containing appropriate reagents) during the reaction or after a reaction cycle and before conducting a new reaction cycle.

The devices described herein are suitable for, but not limited to, conducting nucleic acid amplification reactions requiring temperature cycling. That is, the device is useful for conducting reactions for amplifying nucleic acids that require more than one temperature to conduct portions of the overall reaction such as, for example, denaturing of the nucleic acid(s), annealing of nucleic acid primers to the nucleic acid(s), and polymerization of the nucleic acids (i.e., extension of the nucleic acid primers).

Various nucleic acid amplification methods require cycling of the reaction temperature from a higher denaturing temperature to a lower polymerization temperature, and other methods require cycling of the reaction temperature from a higher denaturing temperature to a lower annealing temperature to a polymerization temperature in between the denaturing and annealing temperatures. Some such nucleic acid amplification reactions include, but are not limited to, polymerase chain reaction (PCR), ligase chain reaction, and transcription-based amplification.

In one particular embodiment, a method for conducting a reaction requiring different temperatures is provided. The method comprises (a) providing at least one reaction droplet to an electrowetting array comprising at least two reaction zones and (b) conducting the reaction by moving, using electrowetting, the at least one reaction droplet through the at least two reaction zones such that a first cycle of the reaction is completed. Each reaction zone has a different temperature needed for the reaction. The reaction droplet comprises reagents needed to effect the reaction. Step (b) may optionally be repeated in order to conduct further cycles of the reaction.

In another particular embodiment, a method for conducting a nucleic acid amplification reaction requiring different temperatures is provided. The method comprises (a) providing at least one reaction droplet to an electrowetting array comprising at least two reaction zones and (b) conducting the nucleic acid amplification reaction by moving, using electrowetting, the at least one reaction droplet through the at least two reaction zones such that a first cycle of the nucleic acid amplification reaction is completed. Each reaction zone has a different temperature needed for the nucleic acid amplification reaction. The reaction droplet comprises a nucleic acid of interest and reagents needed to effect amplification of the nucleic acid. Such reagents may include appropriate nucleic acid primers, nucleotides, enzymes (e.g., polymerase), and other agents. Step (b) may optionally be repeated in order to conduct further cycles of the nucleic acid amplification reaction.

In a further embodiment, another method for amplifying a nucleic acid of interest is provided. The method comprises the steps of (a) providing at least one reaction droplet to an electrowetting array, the reaction droplet comprising a nucleic acid of interest and reagents needed to effect amplification of the nucleic acid, the reagents including nucleic acid primers; (b) moving the droplet(s), using electrowetting, through a first reaction zone of the electrowetting array having a first temperature such that the nucleic acid of interest is denatured; (c) moving the droplet(s), using electrowetting, through a second reaction zone of the electrowetting array having a second temperature such that the primers are annealed to the nucleic acid of interest; and (d) moving the droplet(s), using electrowetting, through a third reaction zone of the electrowetting array having a third temperature such that extension of the nucleic acid primers occurs, thus amplifying the nucleic acid of interest. Steps (b), (c), and (d) may optionally be repeated in order to conduct further cycles of the nucleic acid amplification reaction.

In yet another embodiment, another method for amplifying a nucleic acid of interest is provided comprising the steps of: (a) providing at least one reaction droplet to an electrowetting array, the reaction droplet comprising a nucleic acid of interest and reagents needed to effect amplification of the nucleic acid, the reagents including nucleic acid primers; (b) moving the droplet(s), using electrowetting, through a first reaction zone of the electrowetting array having a first temperature such that the nucleic acid of interest is denatured; (c) moving the droplet(s), using electrowetting, through a second reaction zone of the electrowetting array having a second temperature such that the primers are annealed to the nucleic acid of interest and such that extension of the nucleic acid primers occurs, thus amplifying the nucleic acid of interest. Steps (b) and (c) may optionally be repeated in order to conduct further cycles of the nucleic acid amplification reaction.

When the methods are used to conduct PCR, the reagents in the reaction droplets may include deoxynucleoside triphosphates, nucleic acid primers, and a polymerase such as, for example, a thermostable polymerase such as Taq DNA polymerase.

Illustrative Embodiment

A method is disclosed for conducting chemical or biochemical reactions at various temperatures by moving multiple reaction droplets through parts of a housing kept at desired temperatures, with or without them moving through a detection site at desired time points. The device provided for this purpose comprises path(s) for moving the reactions through the zones having controlled temperature, optional detection sites, and optional return paths for repeating a temperature cycle a desired number of times.

Figure 2:
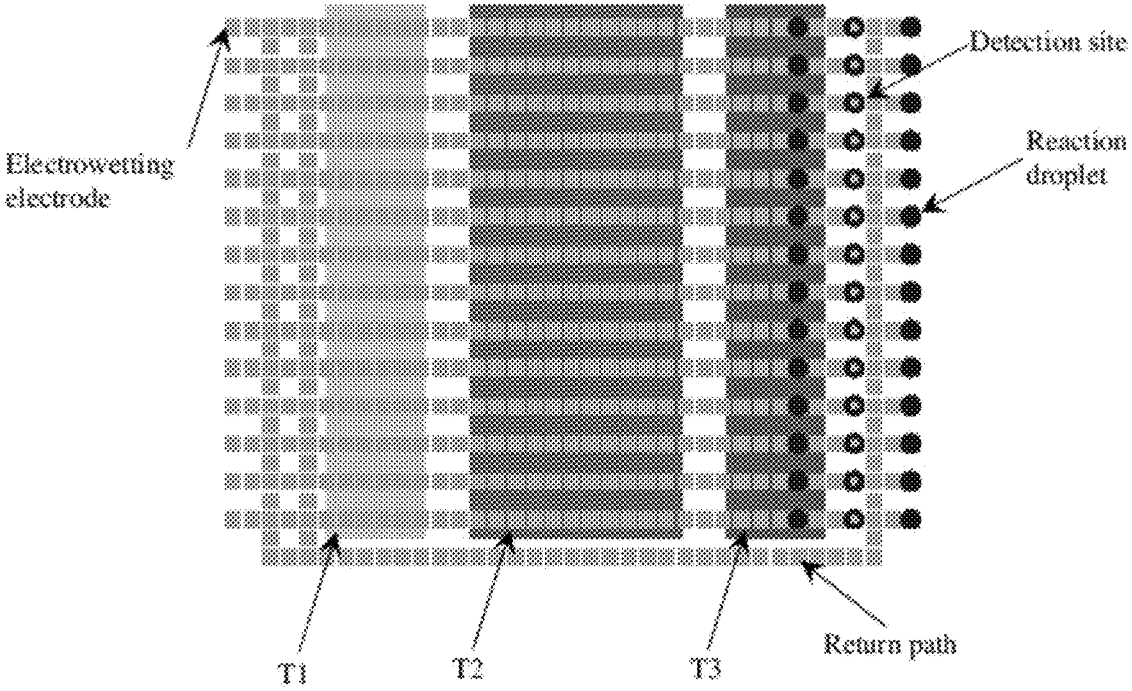
FIG. 2 illustrates an embodiment of a device for conducting real-time polymerase chain reaction using an electrowetting array.

A particular embodiment for realizing real-time PCR is shown in FIG. 2. As shown in FIG. 2, fourteen parallel lines of electrowetting control electrodes provide actuation for moving reaction droplets through three temperature zones. Each path is initially loaded with up to ten PCR reaction droplets. Each of the paths passes through a dedicated detection site as the droplets exit the last temperature-controlled zone. Fluorescence measurements are taken, and then a particular droplet is either discarded or returned to the first temperature zone using a return path. In this particular layout, a single return path is utilized for all fourteen active paths. Preferably, this arrangement is used when the return loop path can be operated at higher throughput than each of the paths through temperature-controlled zones. For example, if droplets are moved from one electrode to the next at 20 Hz, the matching switching frequency for fourteen forward paths and a single return path will be 280 Hz. Preferably also, either before or after the forward paths, or at both ends, provisions are made to reorder the reaction droplets so they enter and exit each cycle in exactly the same sequence. This, in particular, is useful for quantitative PCR (when all reactions should be exposed to very similar, ideally identical, temperature histories).

Methods and Devices Using Other Fluidic or Microfluidic Actuators

In addition to using electrowetting arrays and electrodes in order to actuate the reaction droplets through the reaction zones on the apparatus, other actuation means may be used with the devices and methods described herein. That is, any mechanism for actuating reaction droplets or reaction volumes may be used in the device and methods described herein including, but not limited to, thermal actuators, bubble-based actuators, and microvalve-based actuators. The description of the devices and methods herein where electrowetting is used to manipulate the liquid to conduct the reaction is equally applicable to devices and methods using other actuation means.

Thus, a device for conducting chemical or biochemical reactions that requires multiple reaction temperatures may comprise a microfluidics apparatus comprising at least one reaction path that travels through at least two reactions zones on the device. The device may include one or more detection sites and one or more return paths. The device further comprises means for actuating a reaction droplet or a reaction volume through the reaction path(s), detection site(s), and/or return path(s), and such reaction path(s), detection site(s), and/or return path(s) of the device may be fluidly connected in various ways.

In one embodiment, the device includes multiple reaction paths that travel through at least two reaction zones, wherein each reaction path may include multiple reaction droplets/volumes. In another embodiment, the device includes at least one detection site in or after the one or more reaction paths. In such an embodiment, the detection site(s) and one or more of the reaction paths may be fluidly connected.

As described above, the reaction paths may have various geometrical configurations. For example, the reaction paths may be a circular path comprising at least two reaction zones, a linear path that crosses at least two reaction zones, or other shaped paths.

The devices may also comprise a return path from the end of the reaction path or from the detection site (if the device includes a detection site after the end of the reaction path) to the beginning of the same reaction path (or to a new, identical reaction path) such that multiple cycles of the reaction may be conducted using the same reagents. That is, the device may contain a return path such that multiple reaction cycles may be conducted using a loop path or a meandering path for the total path of the reaction droplets/volumes. The return path may go through one or more of the reaction zones or may entirely bypass the reaction zones. In addition, the return path may have a substantially constant temperature (different from or identical to one of the temperatures maintained in the reaction zones) that is maintained by appropriate heating or cooling mechanisms. In addition, the return path may be operated such that reaction droplets/volumes are returned to the beginning of the same or a new reaction path faster than the time the reaction droplets/volumes spend in the reaction path.

When multiple reaction paths are contained in a device, there may be multiple return paths (e.g., one return path for each reaction path) or there may be less return paths than reaction paths (e.g., only one return path). When there are less return paths than reaction paths, the droplets/volumes may be manipulated on the apparatus such that the reaction droplets/volumes that traveled through a particular path on the first reaction cycle are returned to the identical reaction path for the second reaction cycle, therefore allowing results of each progressive cycle for a particular reaction droplet/volume to be compared to the results of the previous cycles for the same reaction droplet/volume.

In other embodiments, the reaction droplets/volumes may be moved to the beginning of the same reaction path without a return path in order to perform cycles of the same reaction. Such a return path may not be needed where the reaction path and any detection site form a loop, or where the reaction path and any detection site do not form a loop (e.g., a linear path)

and the reaction droplets/volumes are moved in the opposite direction along the same path to return them to the beginning of the same reaction path.

Multiple reaction volumes/droplets may be simultaneously moved through the microfluidics apparatus. In addition, multiple reaction paths may be used having multiple reaction volumes/droplets.

In one particular embodiment, the device comprises multiple reaction paths, at least one detection site either in or after one of the reaction paths, and at least one return path. In such embodiments, when one return path is used, the multiple reaction paths, the at least one detection site, and the return paths may be fluidly connected to form a loop. When multiple return paths are used, multiple loops may be formed.

As also described above, the methods of conducting chemical or biochemical reactions that require multiple reaction temperatures comprise providing at least one reaction droplet/volume to a microfluidics apparatus described herein and then conducting the reaction by moving, using any actuation means, the at least one reaction droplet/volume through the at least two reaction zones. The at least two reaction zones are maintained at the different temperatures needed for the reaction. If desired, the reaction may be repeated with the same reaction droplet by again moving, using the actuation means, the at least one reaction droplet through the at least two reaction zones. Such repetition may be desired where multiple reaction cycles are needed or preferred for a particular reaction.

While the invention has been described in detail and with reference to specific embodiments thereof, it will be apparent to one skilled in the art that various changes and modifications can be made without departing from the spirit and scope of the invention.

We claim:

1. A method of dispensing liquid, the method comprising:

(a) providing an electrowetting device comprising a first substrate and a second substrate spaced apart to form a gap, and an electrowetting array comprising a plurality of electrowetting electrodes on opposite sides of the gap;

(b) transporting a droplet between at least two reaction zones maintained at different temperatures in the gap to produce a thermal cycled droplet, wherein the droplet moves along the gap by electrowetting caused by the droplet contacting the electrodes on the opposite sides of the gap;

(c) positioning the thermal cycled droplet at a specific locus in the gap using the electrowetting array to produce a repositioned droplet; and (d) dispensing the repositioned droplet at the specific locus through a hole in a housing or substrate of the electrowetting device.

2. The method of claim 1 wherein the dispensing comprises using pressure for dispensing the droplet through the hole.

3. The method of claim 1 wherein the dispensing comprises using suction for dispensing the droplet through the hole.

4. The method of claim 1 wherein the dispensing comprises using a capillary for dispensing the droplet through the hole.

5. The method of claim 1 wherein the dispensing comprises using a pipette for dispensing the droplet through the hole.

6. The method of claim 1 wherein the droplet comprises a reaction droplet.

7. The method of claim 1 wherein the droplet comprises DNA.

8. The method of claim 1 wherein the droplet comprises PCR reagents.

9. The method of claim 1, wherein the gap comprises a filler fluid and the droplet is immiscible with the filler fluid comprising an oil.

10. The method of claim 9, wherein the oil comprises a silicone oil.

11. A method of withdrawing liquid, the method comprising:

(a) providing an electrowetting device comprising a first substrate and a second substrate spaced apart to form a gap, and an electrowetting array comprising a plurality of electrowetting electrodes on opposite sides of the gap;

(b) transporting a droplet between at least two reaction zones maintained at different temperatures in the gap to produce a thermal cycled droplet, wherein the droplet moves along the gap by electrowetting caused by the droplet contacting the electrodes on the opposite sides of the gap;

(c) positioning the thermal cycled droplet at a specific locus in the gap using the electrowetting array to produce a repositioned droplet; and (d) withdrawing the repositioned droplet from the specific locus through a hole in a housing or substrate of the electrowetting device.

12. The method of claim 11 wherein the withdrawing comprises using pressure for withdrawing the droplet through the hole.

13. The method of claim 11 wherein the withdrawing comprises using suction for withdrawing the droplet through the hole.

14. The method of claim 11 wherein the withdrawing comprises using a capillary for withdrawing the droplet through the hole.

15. The method of claim 11 wherein the withdrawing comprises using a pipette for withdrawing the droplet through the hole.

16. The method of claim 11 wherein the droplet comprises a reaction droplet.

17. The method of claim 11 wherein the droplet comprises DNA.

18. The method of claim 11 wherein the droplet comprises PCR reagents.

19. The method of claim 11, wherein the gap comprises a filler fluid and the droplet is immiscible with the filler fluid comprising an oil.

20. The method of claim 19, wherein the oil comprises a silicone oil.

* * * * *